United States Patent [19]

Harju-Jeanty et al.

[11] Patent Number: 5,747,417
[45] Date of Patent: May 5, 1998

[54] METHOD FOR PRODUCING PESTICIDE COMPOSITION

[75] Inventors: Pontus Harju-Jeanty, Mustasaari; Torbjörn Ahlskog, Vaasa, both of Finland

[73] Assignee: Hoechst Schering AgrEvo GmbH, Germany

[21] Appl. No.: 700,401

[22] PCT Filed: Feb. 28, 1995

[86] PCT No.: PCT/FI95/00108

§ 371 Date: Aug. 29, 1996

§ 102(e) Date: Aug. 29, 1996

[87] PCT Pub. No.: WO95/23505

PCT Pub. Date: Sep. 8, 1995

[30] Foreign Application Priority Data

Mar. 1, 1994 [FI] Finland ................................ 940968

[51] Int. Cl.⁶ ........................... A01N 25/04; A01N 47/22
[52] U.S. Cl. ........................... 504/116; 504/143; 504/301
[58] Field of Search ........................ 504/301, 116, 504/143

[56] References Cited

U.S. PATENT DOCUMENTS

| | | | |
|---|---|---|---|
| 4,767,448 | 8/1988 | Nielsen | 71/111 |
| 5,178,871 | 1/1993 | Thill | 424/405 |
| 5,321,049 | 6/1994 | Smith et al. | 514/772.6 |
| 5,362,707 | 11/1994 | Fiard et al. | 504/234 |

FOREIGN PATENT DOCUMENTS

| | | |
|---|---|---|
| 0124878 | 11/1984 | European Pat. Off. . |
| 0214843 | 3/1987 | European Pat. Off. . |
| 0242888 | 10/1987 | European Pat. Off. . |
| 3319921 | 12/1984 | Germany . |
| 8705778 | 10/1987 | WIPO . |
| 9007272 | 7/1990 | WIPO . |

*Primary Examiner*—S. Mark Clardy
*Attorney, Agent, or Firm*—Ostrolenk, Faber, Gerb & Soffen, LLP

[57] ABSTRACT

A production method for water-based pesticide composition in which a high power dispersing machine and the tearing mixer blade thereof are used for emulsifying oil. With the method of the invention, storage stability, mixability properties of the product, as well as economy are improved.

6 Claims, No Drawings

METHOD FOR PRODUCING PESTICIDE COMPOSITION

This application has been filed under 35 USC 371 as the national stage of international application PCT/FI95/00108 filed Feb. 28, 1995.

The present invention relates to a method for producing suspension pesticide compositions, said compositions in the form of an effective agent may contain carbamoyl-oxyphenyl carbamates, surfactants, suspending agents, known as such in the art, water, and possibly some other additives, such as organic solvents, stabilizers, defoaming, thickening and defreezing agents, dyes and preservatives.

The pesticid compositions can roughly be divided into two main categories: solid and liquid formulations. The selection is primarily affected by the solubility properties of the effective agent and on the other hand, the biological effect of the product. Certain effective agents are so poorly soluble that in practice it is not possible to provide sufficiently concentrated, genuine, liquid formulations therefrom.

In such an instance, the only possibility to produce a formulation are solid products or a liquid suspension concentrate in which the effective agent is still present as solid particles suspended in water or some other carrier agent.

As regards the user and the environment, a genuine aqueous solution would be most advantageous, but the poor solubility of the effective agent or decomposition in water often forms an obstacle for the use of this product form.

Since water cannot be used as a solvent, organic solvents have to be adopted. By adding emulsifying agents, the product becomes an emulsion concentrate emulsifying with water. A drawback of said formulations is the toxicity and inflammability of organic solvents, and sometimes difficulties in producing a permanent non-crystallized emulsion from a product with water.

The product forms in which the effective agents are not in dissolved form are advantageous as such because in such instances problems related to toxicity, inflammability, packaging materials and storage are in general avoided. However, their biological effect is often insufficient because, especially concerning leaf-affecting herbicides, penetrating ability and translocation ability within a plant is required in order to provide adequate biological effect. Also the hydrolytic decomposition is often a problem. The effective agent in molecular form possesses in a genuine liquid the ability of penetrating the wax and cuticle layers more efficiently than a solid particle. Therefore, the non-soluble effective agent particles should be ground as fine as possible and their penetration and translocation abilities should be improved with oils, organic solvent additions and surfactants. Air jet and pearl mills are used in grindings in order to provide as finely powdered effective agent as possible, preferably of the order of magnitude 1 to 5 microns, both for securing the biological effect and, in suspension concentrates, also for improving storage stability.

In order to inhibit sedimentation of the solid ingredients in suspension products, various additives must be added, besides the carrier liquid, such as dispersing and suspending agents and frequently also wetting, defreezing, defoaming and preservative agents. For providing good storage stability, viscosity of a suspension must often be increased with thickening agents.

It is known in the art that carbamoyl-oxyphenyl carbamates, the most significant among which are methyl-3-m-tolyl-carbamoyl-oxyphenylcarbamate, generally called phenmedipham, and ethyl-3-phenylcarbamoyl-oxyphenylcarbamate, generally called desmedipham (BP 679283)

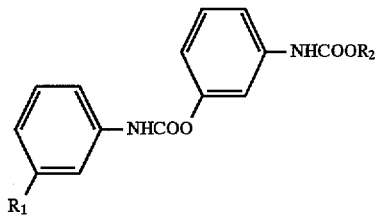

where $R_1$ and $R_2$ are $CH_3$ or $R_1$ is H and $R_2$ is $CH_2CH_3$, are selective and good concerning their herbicide properties. Said effective agents can be used separately or in blends with each other and/or together with other pesticides particularly as a herbicide of sugar beet.

Conventionally the above-mentioned effective agents have been formulated into emulsion concentrates. But since there has been a general tendency to avoid organic solvents, and since phenmedipham is easily crystallized when diluting said formulations in water, the object of the present invention has been to produce suspension concentrates from these effective agents.

It is known in the art to produce carbamoyl-oxyphenyl-carbamates as oil-based (EP-242 888) or water-based (EP-299 961) suspension concentrates in which the effective agents are in solid state finely ground and dispersed by means of surfactants either into aqueous or oil phase. Particularly the carbamoyl-oxyphenyl carbamates while in solid state require oily products and/or organic solvents, as well as surfactants to ensure the biological effect. In oil-based suspension concentrates, the oily liquids are used as carrier agents and the potential water is emulsified in oil phase as water-in-oil emulsion. Respectively, in water-based suspension concentrates the water is used as the carrier liquid in which the oily components have been emulsified as oil-in-water emulsions. In both instances, the product is, however, required to be water-mixable, whereby the oily components form an oil-in-water emulsion. Such dilution carried out by the farmer is of the order 1 part product per 20 to 200 parts water. The effective agents are finely ground, preferably below 5 μm, and dispersed either in oil or water phase. Grinding is accomplished as dry or wet grinding in an air-jet mill, respectively pearl mill.

In the carrier agent the surfactants, dispersing agents for solid effective agent particles are added, and emulsifiers either for water or oily raw materials and for emulsification of the end product, as well as other potential additives, such as stabilizing agents, to bring the acidity of the product to level pH 3-5, to inhibit decomposition of carbamoyl-oxyphenyl-carbamates, and thickeners to improve physical storage stability.

Drawbacks of oil-based suspension concentrates include poor storage stabilities of the products, a need to use great quantities of emulsifiers to correspond to the need of energy what emulsification of the products in a farmer's spray to become an oil-in-water emulsion requires, at least 10% and usually over 20%, and the poor mixability properties of products with other products in aqueous dilutions in the farmer's spray. Because of said factors, there are examples of products which have had to be withdrawn from the market.

Although water-based suspension concentrates with oily components emulsified in water phase are in general superior to oil-based suspension concentrates as regards storage and mix-ability properties, also said concentrates require greater, at least over 5%, and usually over 10% surfactant quantities to render emulsification of oils and dispersion of solid effective agents in water possible. The surfactants used for such purposes are costly, and therefore, increase product prices. The amount of oily agents in a product is preferably over 10%, most commonly over 20%, to achieve a competitive biological effect.

A common feature of both of the suspension concentrates is the roughness of emulsion drops of oily components either as early as in the products or, at the latest, in the farmer's spray. It is known in the art that reducing the size of emulsion drops, the stability of the product can be enhanced. This can be affected by choosing optimal emulsifiers and, above all, a right hydrophilic-lipophilic balance, HLB, for the emulsifiers employed, e.g. about 10 to 12 for paraffine mineral oils when an oil-in-water emulsion is in question. It is also known in the art that by carrying out emulsification at about phase inversion temperature, that is, at a temparature at which the water/oil and oil/water emulsions are inverse, a smaller emulsion drop size is achieved, which also remains when the emulsion is cooled.

Surprisingly, it has now been found that by producing oil containing water-based pesticide compositions in which the oil part is emulsified separately in a high power dispersing machines, significant improvements are gained as regards the storage and mixability properties, and the amounts of emulsifiers can be reduced to a considerable degree, therethrough improving the economy of the products.

The products produced with the method of the invention include in general 10 to 80% effective agents, preferably 15 to 50%, oily products 5 to 80%, preferably 20 to 60%, and water 5 to 80%, preferably 20 to 60%. As taught by the invention, the oil is emulsified separately with a high power dispersing machines into aqueous phase, whereby emulsion drops are produced, the mean size thereof being 1 to 10 μm, preferably below 5 μm. In such instance, the quantities of surfactants may be less than 5% in an end product.

The essential characteristic features of the invention are presented in the accompanying claims.

With high power dispersing machines with which velocities even up to thousands of revolutions per minute are achieved, or with the mixer blades whereof, preferably about 10 to 20 m/s circumferential speeds are achieved, such oil-in-water emulsion drop sizes are obtained which on average are below 5 μm when the oily agent is conducted to the rotating mixer blade or to the immediate vicinity thereof. In this manner, very high quantities of oil can be included in the end product, up to about 80%, and the amount of emulsifier can be below 5%, preferably 0.5 to 3%. Mechanical friction and kinetic energy of the blades and of the high speed of rotation can be stored in the product so that the above-mentioned advantages are gained. Otherwise, an equivalent amount of energy has to be stored in the emulsifiers so that a farmer, while carrying out dilution in water in his spray, would be able to make a good and stable emulsion in water. However, the sprays used in agriculture are not provided with efficient mixers but with simple circulation pumps with which the drop size of emulsions cannot be affected. This results in a rough emulsion being more labile than fine emulsion. Said drawback becomes emphasized significantly in the mixtures to be produced in the sprays in which other products are used together with carbamoyl-oxyphenyl carbamate products, the surfactant components whereof being more readily capable of shaking a poor emulsion. In practice, the situation is just like this. It occurs very rarely that a farmer would use solely carbamoyl-oxyphenyl carbamate products, instead, he mixes simultanously other herbicides in his spray, such as ethofumesate, metamitron, chloridazon, lenacil, pyridate, metholachlor, EPTC, quinmerac, cycloate, chlopyralide, fluroxypyr, alloxydim-sodium, setoxydime, cycloxydim, fluazifop buthyl, and sulphonyl-urea herbicides. Also insecticides, plant disease killers, growth regulators and fertilizisers are often included in the same spray.

In suspension concentrate products produced with the method of the invention, effective agents include carbamoyl-oxyphenyl-carbamates, particularly phenmedipham and desmedipham, but it is self-evident that one and same product may include also other herbicides, insecticides, plant disease killers and/or growth regulators. Particularly useful in widening the weed-prevention spectrum of sugar beets are etofumesate, metamitron, chloridazon, lenacil, pyridate, metholachlor, trichloracetic acid, EPTC, quinmerac, cycloate, chlopyralide, fluroxypyr, benzthiazuron, chlorpropham, fenuron, isocarbimide, propham, trifluraline, alloxydim-sodium, setoxydime, cycloxydim, diallate, fluazifop-buthyl, triallate, dalapon, propaquizafob, and sulphonyl urea herbicides. Conventional insecticides for beets are phosphoric acid esters, organochlorine compounds, carbamates, pyrethrines and pyrethroids. Common plant disease killers include benzimidazols, triazols, carbamates, triphenyl tin compounds and sulphur compounds. Growth regulators used are e.g. naphtalene acetic acid.

Pesticide suspension concentrates usually contain effective agents in the order of magnitude of 10 to 80%, and preferably 15 to 50%. The end products are diluted while being extruded into water.

Surfactants are used to improve dispersion, suspension stability, wetting ability, penetration and translocation, to emulsify oil in the concentrate, and to provide the mixing ability and suspension/emulsion stability of a product in an operating dilution.

As oils are used e.g. mineral oil, plant oil, water-nonsoluble alcohols, acids, ketones, ethers, esters, and halogenated compounds thereof, and glycols either alone or as mixtures. Also other organic solvents may be contained in a product. When a product containing carbamoyl-oxyphenyl carbamate is in question, it is useful to add oil about 5 to 80 per cent by weight, preferably about 20 to 60 w %, of the product in the formulation.

As surfactants, anionic, cationic and non-ionic, and ampholytic surfactants and mixtures thereof can be used. Such agents are e.g. alkyl sulphates and their derivatives, sulphonic acid compounds and sulphonate compounds, phosphoric acid esters and their salts, polyethoxylated amines, amides and fatty acids, alkenoxilated phenols and alkanols, polyglycol ethers, fat-alcohol alkene oxide concentrates, alkyl amino acids, imidazoline amphotensides, and various block copolymers. The total proportion of surfactants in a product according to the present invention can be below 5% so that merely 0.5 to 3% emulsifier may suffice in emulsifying the oil.

Said suspension concentrates may also contain other additives such as water mixing and/or water soluble carrier and/or deflocculation agents (e.g. kaolin, lignin compounds), defoaming agents (e.g. silicon-based), thickening agents (e.g. cellulose derivatives), defreezing agents (e.g. ethylene glycol), organic dissolvents (e.g. kerosen), dyes (e.g. azo dyes), preservatives (e.g. formalin biocide, particularly if the product contains organic suspension agents and thickeners, and e.g. butylated hydroxytoluene antioxidant, particularly if the product contains plant oil and fertilizers (e.g. urea)).

When a product contains one or more carbamoyl-oxyphenyl-carbamate as effective agent, the acidity of the product can be regulated, to be preferably below pH 5 with a stabilizer (e.g. citric acid).

Products as objects of the present invention can be used both before and after plantation of a domestic plant. However, it is most common to use carbamoyl-oxyphenyl carbamates either alone or as mixtures after plantation of beets, whereby the weeds to be prevented are there. An appropriate amount of an effective agent per cultivated hectare and surface area to be sprayed is 0.1 to 1 kg, depending on whether an individual or several consecutive sprayings are carried out, and on mixing proportions.

An essential feature of the method of the present invention is emulsification of oil with the aid of high power dispersing machines (e.g. Ultra Turrax, Mastermix, Dispax, Ystral) in a water-emulsifier mixture. When oil is added either in a water-emulsifier premixture or in an emulsifier-suspension mixture already containing effective agents to the immediate vicinity of the tearing blade of the high power dispersing machine, for instance by conducting it with a feed pipe, very high quantities of oil can be emulsified in the end product, up to 80%, with the aid of very low emulsifier quantities, that is, below 5%, in great batches of thousands of liters. The non-soluble effective agents can be ground either as wet-grinding in a pearl mill (e.g. Dyno, Drais) or as dry grinding in an air-jet mill (e.g. Alpine, Chrispro), and mixed with conventional mixers with other additives into a carrier liquid. A most preferred end result is obtained when an end product is produced in steps so that the effective agents are dispersed separately with dispersing agents in aqueous phase into a suspension premixture and oil separately with the high power dispersing machine in an emulsifier-water mixture into oil-in-water emulsion. Finally, said premixtures are combined by conventional slow mixing into an end product. In said fashion, highly stable suspension emulsions are produced, the storage and mixing properties thereof being superior and the economic aspect thereof being more advantageous than before due to the low emulsifier content.

The invention is clarified below more closely with the aid of examples.

EXAMPLE 1

I Oil-in-water emulsion was prepared using the method of the invention in which the oil was emulsified in water with a high-power dispersing machine (Ystral X 50/10 provided with a mixer blade 41 G, 4000 to 5000 rpm, circumferential speed about 7 to 9 m/s).

II Oil-in-water emulsion was prepared with the same raw materials using propeller agitator (Morat, 1500 to 2000 rpm, circumferential speed about 4–5 m/s).

| | |
|---|---|
| Water | 26.6% |
| Emulsifier | 1.8% |
| Oil | 71.6% |
| | 100.0% |

| | Product I | Product II |
|---|---|---|
| Mean particle size (μm) | 4.3 | 32.6 |

The superiority of the high power dispersing machine can thus be clearly proved in producing emulsions in comparison with propeller agitator.

The stability with product II is poor.

EXAMPLE 2

I Premix A and Premix B were prepared separately, whereafter the premixtures were combined and a thickening agent and dispersing agent were mixed therein.

The raw materials of Premix A were mixed with a conventional propeller agitator whereafter the mixture was ground in a pearl mill (Dyno KDL-Special) into mean particle size of below 3 μm.

Premix B was prepared in another container adding oil slowly with the aid of the high power dispersing machine (Ystral X 50/10 provided with a mixer blade 41 G) into water-emulsifier mixture.

Thickening agent, end dispersion agent and Premix B were added into Premix A, whereafter the mixture was homogenized with the high power dispersing machine.

II Preparation as in alternative I, but the end mixture Premix A+thickening agent+end dispersion agent+Premix B was carried out with a conventional propeller mixer (Morat, 1500–2000 rpm).

III Premix A was prepared as in alternative I, whereafter the thickening agent, end dispersion agent, the water of Premix B and emulsifier were added and in the end, oil was emulsified with the aid of the high power dispersing machine into the mixture.

IV Premix A was prepared as in alternative I but Premix B with a conventional propeller mixer (Morat, 1500–2000 rpm). Also the end mixing was accomplished with propeller mixer.

| Premix A | | |
|---|---|---|
| Water | 46.5 | 19.4 |
| Preservative | 0.01 | 0.005 |
| Defoaming agent | 0.3 | 0.1 |
| Defreezing agent | 7.8 | 3.2 |
| Stabilizer | 0.8 | 0.3 |
| Dispersion agent | 5.3 | 2.2 |
| Phenmedipham (techn.) | 39.3 | 16.3 |
| | 100.0% | 41.5% |

| Premix B | | |
|---|---|---|
| Water | 26.6 | 15.1 |
| Emulsifier | 1.8 | 1.0 |
| Oil | 71.6 | 40.5 |
| | 100.0% | 56.6% |
| Thickening agent | | 0.4 |
| Dispersion agent | | 1.5 |
| | | 100.0% |

Suspensibility is determined according to CIPAC regulation 161. The test was performed at +30° C., duration 1 hr. The concentration of the dilution was equivalent to utility dilution, that is, in 250 ml hard water (CIPAC MT 18, Standard Water D) 5 g of the formulation was blended. The values in the table are an average of two parallel samples.

The particle size was determined with Coulter LS 130 particle size analyser at +20° C. Prior to said determination, a predilution (about 2 g sample/50 ml water) has been made from sample to be analysed. The particle size have been determined from the predilution according to the instructions. The sizes in the table are the mean values of the particle size distribution.

The viscosities of the samples are determined with Bohlin CS rheometer at +25° C. The samples kept stored have been mixed by turning the sample bottom ten times upside down prior to adding a sample in the sample cup of the rheometer. Before the measurement, the sample was kept 5 minutes immobile in the sample cup. Viscosity was determined with measurement geometry C 25 as a function of the shear rate. In the viscosity run 10 different shear rates were used, and the run was carried out as a cycle, starting at lowest shear rate (0.13 $s_{-1}$), from which gradual transfer to the highest speed (39 $s^{-1}$) was carried out, and finally back to a lower speed. The viscosity values in the table were obtained in the first phase at speed 4.6 $s^{-1}$.

The storage stability (=depositions) have been determined by visual inspection from about 100 ml samples stored at said temperatures. The depositions thus provided are presented as volumetric percentages.

suspended effective agent particles, 1 to 5 μm on average in size, were clearly separable from the emulsion drops, the size of which in product 1 being 2–6 μm on average and in product 2 10 to 50 μm on average.

We claim:

1. A method for preparing oil-in-water herbicide suspensions containing at least one carbamoyl oxyphenyl carbamate herbicide, wherein either: a) oil is emulsified with a water-emulsifier solution, and then mixed with said herbicide, or (b) oil is emulsified with a water-emulsifier-herbicide mixture, characterized in that said emulsifying is performed in a high power dispersing machine with a circumferential blade speed of between about 7 to 20 m/s, such that the mean oil drop size of said emulsion is less than 5 micrometers and wherein the emulsion includes at least one surfactant selected from the group consisting of alkyl sulfates and derivatives thereof, sulfonic acid compounds, sulfonate compounds, phosphoric acid esters and salts, polyethoxylated amines, amides, fatty acids, alkenoxilated phe-

| Formulate | I | | | | II | | | | III | | | |
|---|---|---|---|---|---|---|---|---|---|---|---|---|
| alternatives | — | 2 wks | 1 mnth | 2 mnths | — | 2 wks | 1 mnth | 2 mnths | — | 2 wks | 1 mnth | 2 mnths |
| Suspensibility (%) | 98,0 | 97,6 | 97,9 | 97,8 | 100,6 | 97,8 | 97,8 | 99,1 | 101,4 | 98,8 | 98,6 | 97,7 |
| Means part. size (μm) | 2,8 | 2,9 | 3,5 | 4,4 | 2,9 | 3,7 | 7,8 | 4,1 | 4,3 | 4,5 | 4,9 | 4,9 |
| Viscosity (mPas) | 384 | 292 | 315 | 367 | 348 | 279 | 239 | 251 | 213 | 169 | 168 | 166 |
| Deposition (%) | | | | | | | | | | | | |
| +54° C. | — | — | 1,5 | 8,0 | — | — | 1,0 | 10,0 | — | 9,0 | 13,0 | 16,0 |
| +40° C. | — | — | — | — | — | — | — | — | — | — | 6,0 | 10,0 |
| +20° C. | — | — | — | — | — | — | — | — | — | — | 1,6 | 3,0 |

It can be found in the results that the essential feature is emulsification of oil in water with the aid of a high power dispersing means. There are no differences between alternatives I and II in which the emulsification of oil is performed in separation. Storage stability suffers slightly (Alternative II) when oil is emulsified into an effective agent suspension. Alternative IV, based on product II in Example 1, cannot be implemented in practice because of the non-feasible storage and mixing properties.

EXAMPLE 3

From oil-in-water emulsions I and II of Example 1 respective end products I and II were prepared by mixing a premix A as in Example 2 and additional dispersion agent and thickener. Mixing was carried out with a propeller mixer (Morat, 1500–2000 rpm circumferential speed about 4–5 m/s).

| | Product I | Product II |
|---|---|---|
| Mean particle size (μm) | 5.1 | 10.1 |

Because the mean particle size of the effective agent in Premix A was 2.6 μm, a lower mixture particle size is respectively obtained in product II from emulsion drops and the effective agent particles. The situation was ensured by examining the products under a microscope, whereby the nols and alkanols, polyglycol ethers, fat-alcohol alkene oxide concentrates, alkyl amino acids, imidazoline amphotensides, and block copolymers;

wherein said emulsion does not include a sucroglyceride surfactant.

2. A method according to claim 1, wherein the carbamoyl-oxyphenyl carbamate herbicide is methyl-3-m-tolylcarbamoyl-oxyphenyl carbamate (phenmedipham) or ethyl-3-phenylcarbamoyl-oxyphenyl carbamate (desmedipham).

3. A method according to claim 1, wherein the mean particle size of the carbamoyl-oxyphenyl carbamate herbicide is less than 5 μm.

4. A method according to claim 1, wherein said suspensions comprise 10–80% of carbamoyl-oxyphenyl carbamate herbicide alone or in combination with other herbicides, 5–80% of oil, and 5 to 80% of water, and less than 5% of surfactants.

5. A method according to claim 1, wherein said suspensions comprise 15–50% of carbamoyl-oxyphenyl carbamate herbicide alone or in combination with other herbicides, 20–60% of oil, 20–60% of water, and less than 5% of surfactants.

6. A method according to claim 1, wherein said suspensions are diluted for use as beet herbicides, said dilution being 1 part of said suspension in 20–200 parts of water.

* * * * *